(12) United States Patent
Widder et al.

(10) Patent No.: US 7,754,675 B2
(45) Date of Patent: Jul. 13, 2010

(54) 2-HEPTYLCYCLOPROPYL-1-CARBOXYLIC ACID

(75) Inventors: Sabine Widder, Holzminden (DE); Jan Looft, Holzminden (DE); Armin Van Der Kolk, Much (DE); Tobias Vössing, Beverungen (DE); Wilhelm Pickenhagen, Schweiz (DE); Birgit Kohlenberg, Pegestorf (DE)

(73) Assignee: Symrise GmbH & Co. KG, Holzminden (DE)

( * ) Notice: Subject to any disclaimer, the term of this patent is extended or adjusted under 35 U.S.C. 154(b) by 797 days.

(21) Appl. No.: 10/536,007

(22) PCT Filed: Nov. 19, 2003

(86) PCT No.: PCT/EP03/12927

§ 371 (c)(1),
(2), (4) Date: Nov. 29, 2005

(87) PCT Pub. No.: WO2004/046079

PCT Pub. Date: Jun. 3, 2004

(65) Prior Publication Data

US 2006/0128603 A1    Jun. 15, 2006

(30) Foreign Application Priority Data

Nov. 21, 2002    (DE) ............... 102 54 265

(51) Int. Cl.
*A61K 8/00*     (2006.01)
*A61K 8/18*     (2006.01)
*C07C 61/04*    (2006.01)
*A23L 1/22*     (2006.01)
*A23L 2/56*     (2006.01)
*C07C 61/00*    (2006.01)
*A23L 1/221*    (2006.01)
*A01N 65/00*    (2009.01)

*C09K 15/06*    (2006.01)
*C09K 3/00*     (2006.01)

(52) U.S. Cl. ............. 512/1; 562/506; 562/400; 512/8; 512/22; 512/26; 426/534; 426/535; 426/538; 424/777; 252/183.11; 252/500

(58) Field of Classification Search ............ 562/400, 562/404, 506; 426/5, 8, 534, 3, 535, 538, 426/650; 424/777; 512/1, 8, 22, 26; 252/183.11, 252/500

See application file for complete search history.

(56) References Cited

U.S. PATENT DOCUMENTS

| 2,603,652 | A | * | 7/1952 | Schechter et al. | 560/124 |
|---|---|---|---|---|---|
| 3,282,984 | A | * | 11/1966 | Matsui et al. | 560/124 |
| 3,465,008 | A | * | 9/1969 | Mills | 562/506 |
| 3,527,769 | A | * | 9/1970 | Hirosuke et al. | 549/283 |
| 3,786,052 | A | * | 1/1974 | Martel et al. | 549/499 |
| 3,787,593 | A | * | 1/1974 | Atkins | 426/429 |
| 3,813,432 | A | * | 5/1974 | Heine et al. | 562/501 |
| 3,836,568 | A | * | 9/1974 | Higo et al. | 560/124 |
| 3,926,860 | A | * | 12/1975 | Chappell | 512/8 |
| 4,182,906 | A | * | 1/1980 | Suzukamo et al. | 562/506 |
| 4,236,026 | A | * | 11/1980 | Naumann | 562/401 |
| 6,160,134 | A | * | 12/2000 | Chen et al. | 549/462 |
| 2005/0075393 | A1 | * | 4/2005 | Nishizaki et al. | 514/531 |

FOREIGN PATENT DOCUMENTS

| GB | 1567434 | * | 5/1980 |
|---|---|---|---|
| WO | WO 0250013 | * | 6/2002 |
| WO | WO 0250013 A1 | * | 6/2002 |

* cited by examiner

*Primary Examiner*—Milton I Cano
*Assistant Examiner*—Aaron Greso
(74) *Attorney, Agent, or Firm*—Roylance, Abrams, Berdo & Goodman, L.L.P.

(57) ABSTRACT

Optionally isolated and/or purified enatiomers of 2-heptylcyclopropyl-1-carboxylic acid and mixtures of two, three or all enantiomers of 2-heptylcyclopropyl-1-carboxylic acid are disclosed as perfumes and/or flavourings.

20 Claims, 2 Drawing Sheets

2-HEPTYLCYCLOPROPYL-1-CARBOXYLIC ACID

This application is a 35 USC 371 PCT/EP2003/012927 filed Nov. 29, 2003.

The invention relates to the novel substance 2-heptylcyclopropyl-1-carboxylic acid, its optionally isolated and/or purified enantiomers and mixtures of two, three or all enantiomers of 2-heptylcyclopropyl-1-carboxylic acid.

The invention also relates to perfume compositions and/or flavouring compositions, flavoured foodstuffs, perfumed body care products, cleaning agents or other products not intended for consumption, containing an organoleptically active quantity of at least one enantiomer of 2-heptylcyclopropyl-1-carboxylic acid.

The invention also relates to processes for the production or modification of perfume compositions or flavouring compositions using an organoleptically active quantity of 2-heptylcyclopropyl-1-carboxylic acid as well as processes for the production of the cis and trans isomers of 2-heptylcyclopropyl-1-carboxylic acid.

In perfuming and flavouring practice, there is generally a constant need for synthetic perfumes and flavourings that can be produced favourably and with consistent quality, remain stable on prolonged storage, even in contact with other substances if possible, and have desirable olfactory and/or taste properties. Perfumes should have pleasant fragrance notes that are as close to natural as possible, with sufficient intensity, and should be able to have a favourable effect on cosmetic or technical consumer goods. Flavourings should be well tolerated, reminiscent of typical taste components of popular dishes or even identical with these and should contribute to a positive effect on the taste of foodstuffs, orally administered medicines and the like.

The discovery of perfumes and flavourings that meet these requirements has proved relatively expensive and regularly requires extensive investigations, particularly if interesting, novel perfume notes or taste directions are sought.

The search for suitable perfumes and flavourings is made more difficult for the person skilled in the art by the following facts in particular:

- The mechanisms of perfume and flavour perception are not sufficiently known.
- An objective characterisation of a perfume or flavour is impossible.
- The connections between the perception of perfume and/or flavour on the one hand and the chemical structure of the perfume and/or flavouring on the other hand have not been adequately researched.

Success in the search for suitable perfumes or flavourings thus depends to a considerable extent on the intuition of the searcher.

The present invention was first based on the object of providing novel, interesting perfumes and/or flavourings while respecting the general outline conditions described above. The substances to be provided should offer the perfumer or flavourist a versatile alternative to the perfumes and flavourings used or described up to the present, and in particular should be suitable to exert a positive influence on the overall sensory impression of perfume compositions and/or flavouring compositions, flavoured foodstuffs or perfumed products not intended for consumption.

According to the invention, this object is achieved by an optionally isolated and/or purified enantiomer of 2-heptylcyclopropyl-1-carboxylic acid or by a mixture of two, three or all enantiomers of 2-heptylcyclopropyl-1-carboxylic acid.

The 2-heptylcyclopropyl-1-carboxylic acid according to the invention has now been found in and isolated from oranges. 2-Heptylcyclopropyl-1-carboxylic acid was isolated and identified for the first time in this way using very complex analytical and preparative processes. In total, a 2-heptylcyclopropyl-1-carboxylic acid content of about 1 ppb was found in orange residue, which consisted of only one enantiomer. The (1S,2R) 2-heptylcyclopropyl-1-carboxylic acid (formula C) was identified as the naturally occurring compound.

The starting substance for the isolation was orange residue, a viscous distillation residue obtained from orange peel oil (which corresponds to the proportion of oil found in the oil glands of the citrus peel). Peel oils are important natural starting materials in the creation of flavourings, e.g. for drinks or the citrus flavouring of foodstuffs. The proportion of residue in a peel oil is generally in the range of a few per cent by weight, typically in the range of 1 to 5 wt. %.

In formula A, 2-heptylcyclopropyl-1-carboxylic acid is represented without any information as to the absolute stereochemistry:

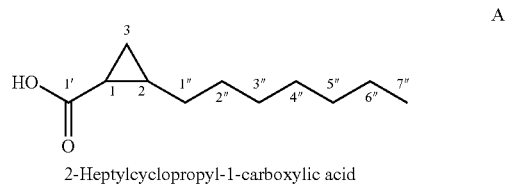

2-Heptylcyclopropyl-1-carboxylic acid      A

2-Heptylcyclopropyl-1-carboxylic acid comprises the isomer cis-2-heptylcyclopropyl-1-carboxylic acid with its enantiomer pair of (1R,2S)-2-heptylcyclopropyl-1-carboxylic acid (represented in formula B) and (1S,2R)-2-heptylcyclopropyl-1-carboxylic acid (represented in formula C)

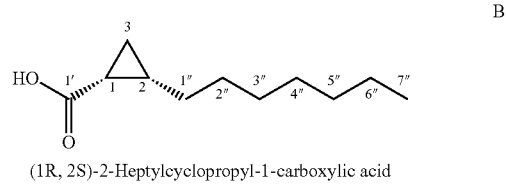

(1R, 2S)-2-Heptylcyclopropyl-1-carboxylic acid      B

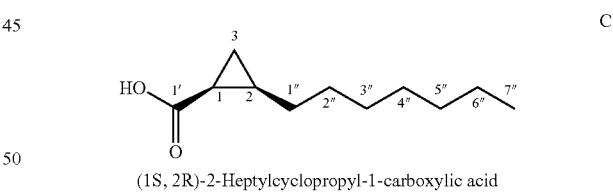

(1S, 2R)-2-Heptylcyclopropyl-1-carboxylic acid      C and the isomer trans-2-heptylcyclopropyl-1-carboxylic acid with its enantiomer pair (1R,2R)-2-heptylcyclopropyl-1-carboxylic acid (illustrated in formula D) and (1S,2S)-2-heptylcyclopropyl-1-carboxylic acid (illustrated in formula E).

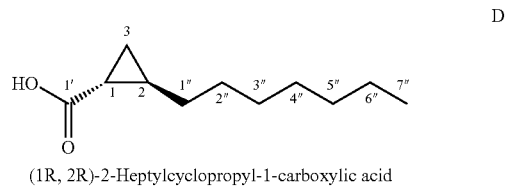

(1R, 2R)-2-Heptylcyclopropyl-1-carboxylic acid      D

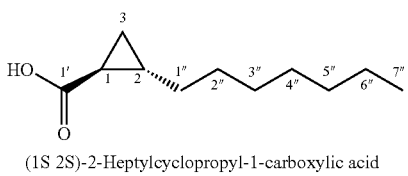

(1S 2S)-2-Heptylcyclopropyl-1-carboxylic acid

The cis and trans isomers are therefore diastereomers, each of which comprises a pair of enantiomers of 2-heptylcyclopropyl-1-carboxylic acid.

Surprisingly, it has been shown that the (four in total) enantiomers of 2-heptylcyclopropyl-1-carboxylic acid possess a very interesting flavour note and/or a very interesting odour. The enantiomers of the cis isomer give odour notes that can be described as follows: woody, balsamic, incense-like, green, herbal, pith-like, waxy; those of the trans isomer give odour notes that can be described as waxy, fatty, sweet.

Mixtures of two, three or all the enantiomers of 2-heptylcyclopropyl-1-carboxylic acid emphasise or modify, depending on their composition, some aspects of the individual sensory properties of the enantiomers. Depending on the sensory impression desired, the person skilled in the art will adjust the proportions of the individual enantiomers in a mixture.

No indications of the special properties of the enantiomers and enantiomer mixtures according to the invention can be taken from the prior art:

U.S. Pat. No. 3,926,860 discloses cis-2-n-pentylcyclopropyl-1-carboxylic acid as a perfume with patchouli-like, animal and leathery perfume properties.

JP 10-165132 describes cis- and trans-2-n-pentylcyclopropyl-1-carboxylic acid with particular emphasis on the taste effects that can be achieved with these substances.

However, neither of the above documents contains any references to 2-heptylcyclopropyl-1-carboxylic acid, and in particular any references to its special sensory properties.

BRIEF DESCRIPTION OF THE DRAWINGS

Referring now to the attached drawings which form a part of this original disclosure.

Figure 1:
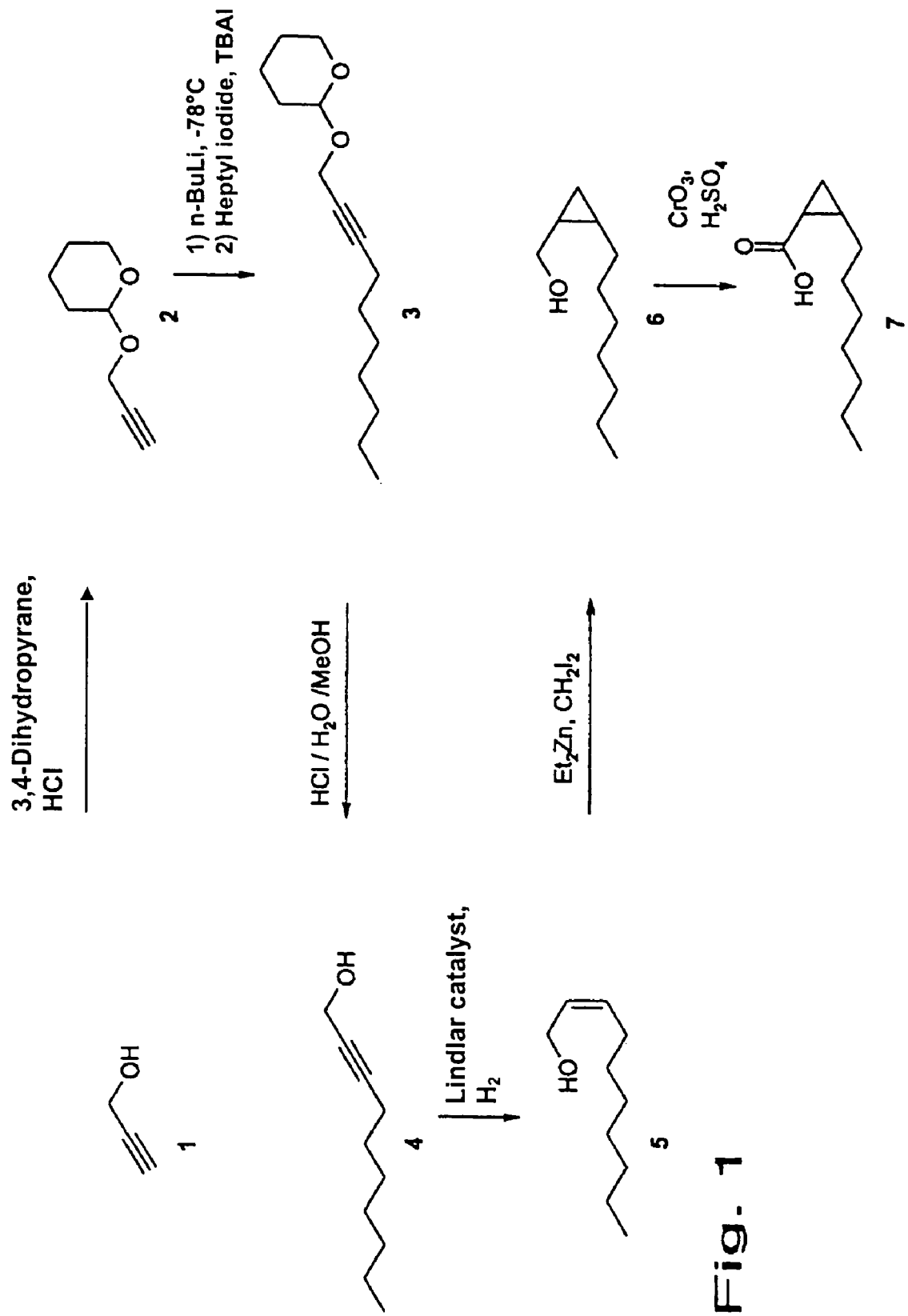
FIG. 1 shows the synthesis of cis-2-heptylcyclopropyl-1-carboxylic acid (7)

Mixtures of the two enantiomers (a) of cis-2-heptylcyclopropyl-1-carboxylic acid or (b) of trans-2-heptylcyclopropyl-1-carboxylic acid are preferably used as a perfume and/or flavouring, preferably little or no trans-2-heptylcyclopropyl-1-carboxylic acid (trans:cis ratio<1:10) being contained in mixture (a) and preferably little or no cis-2-heptylcyclopropyl-1-carboxylic acid (cis:trans ratio<1:10) in mixture (b), to allow the sensory impression to be perceived as clearly as possible.

The mixtures of the enantiomers of trans-2-heptylcyclopropyl-1-carboxylic acid, particularly the racemic mixture, possess a waxy, fatty, sweet perfume note, the individual aspects of which can be particularly emphasised or modified by shifting the enantiomer ratio as appropriate. The odour threshold for the racemic mixture of trans-2-heptylcyclopropyl-1-carboxylic acid is 100 ppb in water (100 µg/l water).

On the other hand, mixtures of the enantiomers of cis-2-heptylcyclopropyl-1-carboxylic acid, particularly the racemic mixture, possess aspects of the perfume notes woody, balsamic, incense-like, green, herbal, pith-like and waxy. Here too, individual aspects of these perfume notes can be emphasised or modified by appropriate adjustment of the ratios of the enantiomers of cis-2-heptylcyclopropyl-1-carboxylic acid. The odour threshold for the racemic mixture of cis-2-heptylcyclopropyl-1-carboxylic acid is 3 ppb in water (3 µg/l water) and is thus extremely low. Mixtures of the enantiomers of cis-2-heptylcyclopropyl-1-carboxylic acid, particularly the racemic mixture, are highly suitable for use in perfume and flavouring formulations. The mixtures impart body and fullness to flavouring formulations and an acid-intensifying effect can be detected. In addition, mixtures of the enantiomers of the cis isomers of 2-heptylcyclopropyl-1-carboxylic acid have a balsamic, peel-like but not aldehydic flavour note. The surprising lack of an aldehydic flavour note represents an interesting special feature, since peel-like flavour notes are otherwise regularly accompanied by an aldehydic note.

Mixtures of the two enantiomers of cis and trans isomers respectively, in which an enantiomeric excess of at least 40% is established, have proved particularly advantageous for emphasising certain flavour impressions or perfume notes. The desired effects could be achieved with particular clarity with such an enantiomeric excess.

The present invention also relates to perfume compositions and/or flavouring compositions containing an organoleptically active quantity of an optionally isolated and/or purified enantiomer or of a mixture of enantiomers of 2-heptylcyclopropyl-1-carboxylic acid. Preferred mixtures are again those of the two enantiomers of cis-2-heptylcyclopropyl-1-carboxylic acid or of trans-2-heptylcyclopropyl-1-carboxylic acid with preferably an enantiomeric excess of at least 40% of one of the two enantiomers.

An organoleptically active quantity of an enantiomer or mixture of enantiomers is present particularly when an organism, especially a human, is able to perceive the sensory action of the relevant enantiomer or mixture of enantiomers using its sense of smell or taste.

Particularly preferred are perfume compositions and flavouring compositions according to the invention containing a proportion of $\geq$0.001 wt. %, preferably $\geq$0.01 wt. %, particularly $\geq$0.05 wt. %, more preferably $\geq$0.1 wt. % and in some cases even $\geq$1 wt. % of an enantiomer according to the invention or of a mixture of enantiomers according to the invention, based on the total mass of the perfume composition or flavouring composition. Such a proportion of an enantiomer according to the invention or of a mixture of enantiomers according to the invention is suitable in a particularly effective manner to exert a positive influence on the overall impression of perfume compositions and/or flavouring compositions, cf. also Example 4 below in this connection.

The invention also relates to flavoured foodstuffs and perfumed body care products, cleaning agents and other products not intended for consumption, each containing an organoleptically active quantity of an enantiomer according to the invention or of a mixture of enantiomers according to the invention.

The flavoured foodstuffs and perfumed body care products, cleaning agents and other products not intended for consumption according to the invention preferably each have a proportion of $\geq$0.01 wt. %, particularly $\geq$0.05 wt. %, more preferably $\geq$0.1 wt. % and in some cases even $\geq$1 wt. % of the perfume and flavouring compositions according to the invention, based on the total mass of the respective flavoured foodstuffs and perfumed body care products, cleaning agents and other products not intended for consumption.

The content of an enantiomer according to the invention or of a mixture of enantiomers according to the invention in the flavoured foodstuffs and perfumed body care products, cleaning agents and other products not intended for consumption is preferably in the range of 0.01 to 500 ppm, particularly preferably in the range of 0.1 to 100 ppm.

Preferred products according to the invention contain a quantity of an enantiomer according to the invention or of a mixture of enantiomers according to the invention in addition to one or more substances from the group consisting of: natural perfume oils; synthetic perfume oils; essential oils; natural plant extracts; alcohols; aldehydes; ketones; esters; lactones; carboxylic acids; detergents; soaps; bath preparations; hair preparations; cosmetic preparations; powders; synthetic carbohydrates; natural carbohydrates; synthetic fats; natural fats; proteins; vitamins.

Another component of the invention is accordingly the use of an enantiomer according to the invention or of a mixture of enantiomers according to the invention as a perfume and/or flavouring.

The use of the enantiomers and mixtures of enantiomers according to the invention as perfumes, particularly as perfumes in the perfume industry, is particularly suitable for cis-2-heptylcyclopropyl-1-carboxylic acid, the odour properties of which are particularly prized by perfumers. The low odour threshold of the cis isomer proves advantageous, as even small quantities of this substance according to the invention are sufficient to produce a desired odour. However, the enantiomers of the trans isomer and mixtures thereof also exhibit excellent sensory properties and quite a low odour threshold, so that they are also highly suitable for use as a perfume.

A corresponding process according to the invention for the production or modification of a perfume or flavouring composition contains the following steps:

preparation of a starting composition and mixing the starting composition with an organoleptically active quantity of an enantiomer or of a mixture of enantiomers according to the invention.

In this way, desired perfume and/or flavour effects can be achieved, e.g. the shifting of an existing flavour impression in a fresher, fruitier, fuller and/or more peel-like direction (cf. also Example 4).

The invention also relates to a process for the selective production of cis- or trans-2-heptylcyclopropyl-1-carboxylic acid, wherein a precursor with a Z- or E-configured double bond is used as the starting substance for establishing the cis or trans configuration of substituents on the cyclopropane ring and this double bond is selectively cyclopropanated. With the said process, the desired cis- or trans-2-heptylcyclopropyl-1-carboxylic acid can be prepared with high selectivity.

The invention also relates to processes for the production of cis-2-heptylcyclopropyl-1-carboxylic acid, in which (a) 2-decyn-1-ol is obtained after chain lengthening of propargyl alcohol, which is then stereoselectively hydrogenated and stereoselectively cyclopropanated, and/or (b) cis-2-heptylcyclopropyl-1-methanol is oxidised to cis-2-heptylcyclopropyl-1-carboxylic acid. The cyclopropanation can optionally take place enantioselectively using chiral auxiliary substances. For the oxidation of heptylcyclopropyl-1-methanol to cis-2-heptylcyclopropyl-1-carboxylic acid, for example, chromium reagents such as chromosulfuric acid can be used, but also processes which employ e.g. the free radical TEMPO.

Also part of the invention are processes in which trans-2-heptylcyclopropyl-1-carboxylic acid is produced by a Wittig-Horner reaction on octanal with subsequent trans-selective cyclopropanation of the 2-(E)-decenoic acid ethyl ester obtained by subsequent basic ester hydrolysis.

The invention also relates to processes for the production of 2-heptylcyclopropyl-1-carboxylic acid, in which the cis and trans compounds are obtained as a mixture. The processes comprise e.g.

(a) The transition-metal-catalysed reaction of 1-nonene with diazoacetate. Achiral compounds, such as rhodium acetate or copper bronze, can be used here, but transition metal complexes with chiral ligands, such as e.g. bisoxazolines or Schiff's bases, are also suitable. The composition of the cis-/trans-2-heptylcyclopropyl-1-carboxylic acid ester mixtures thus obtained can be adjusted by distillation. The cis-/trans-2-heptylcyclopropyl-1-carboxylic acid ester mixtures are saponified to 2-heptylcyclopropyl-1-carboxylic acid. Since the trans-2-heptylcyclopropyl-1-carboxylic acid ester saponifies more rapidly under suitable solvolysis conditions (e.g. aqueous KOH or NaOH in aqueous ethanolic solution), the cis/trans content can also be adjusted in this way.

(b) The reaction of 1,3-dicarboxyl compounds, such as e.g. malonates or Meldrum's acid, with 1,2-disubstituted nonanes, such as e.g. 1,2-dibromononane or 4-heptyl-[1,3,2]dioxathiolane 2,2-dioxide. By selecting suitable chiral 1,2-disubstituted nonanes, the 2-heptylcyclopropyl-1-dicarboxylic acid esters can be obtained in enantiomer-enriched form. The 2-heptylcyclopropyl-1-dicarboxylic acid esters can either be directly decarboxylated and then saponified or first saponified and the resulting 2-heptylcyclopropyl-1-dicarboxylic acid then decarboxylated. The decarboxylation of the corresponding monoesters or of mixed esters is also possible.

The composition of the cis-/trans-2-heptylcyclopropyl-1-carboxylic acid mixtures produced by these processes can be adjusted by distillation.

A further component of the invention is to enrich individual enantiomers in mixtures containing more than one enantiomer of 2-heptylcyclopropyl-1-carboxylic acid, preferably in mixtures of the respective enantiomers of cis- or of trans-2-heptylcyclopropyl-1-carboxylic acid, and/or to separate the enantiomers of one of these from one another. The person skilled in the art will select suitable methods of achieving this, such as e.g. separation by chiral gas chromatography.

The invention is explained below on the basis of examples with reference to the attached figures. The numbers in brackets after the substance names correspond to the numbers in FIGS. 1 and 2.

EXAMPLE 1

Synthesis of cis-2-heptylcyclopropyl-1-carboxylic acid (7)

The synthesis is illustrated diagrammatically in FIG. 1.

Propargyl alcohol (2-propyn-1-ol) is protected as THP ether (tetrahydropyranyl ether), lithiated with n-BuLi and extended by one $C_7$ unit with heptyl iodide. The 2-decyn-1-ol is deprotected by transacetalisation to methanol. The cis configuration of the substituents on the cyclopropane ring of cis-2-heptylcyclopropyl-1-methanol is guaranteed by the syn-selective (cis-selective) hydrogenation on a Lindlar catalyst and subsequent syn-selective (cis-selective) cyclopropanation with a modified Simmons-Smith method. Selectivity of the reactions: hydrogenation on Lindlar catalyst: E. N. Marvell, T. Li, *Synthesis* 1973, 457-468; Simmons-Smith reaction: H. E. Simmons, E. P. Blanchard, R. D. Smith, *J. Am.*

*Chem. Soc.* 1964, 86, 1347-1356). This is followed by oxidation to cis-2-heptylcyclopropyl-1-carboxylic acid with chromosulfuric acid.

2-Propynyltetrahydro-2H-pyran-2-yl ether (2)

1 ml of HCl (32%) was added to 25.2 g (0.3 mol) 3,4-dihydropyrane at 5° C., with stirring. 11.2 g (11.8 ml, 0.2 mol) of 2-propyn-1-ol (1) were metered in within 30 min, in such a way that the temperature did not exceed 10° C. The mixture was stirred for 2 h at 5° C. and 18 h at room temperature. 100 ml of diethyl ether were added and washing was performed twice with 20 ml of saturated sodium hydrogen carbonate solution and 20 ml of saturated common salt solution each time. Drying was performed over sodium sulfate and the ether was distilled off using a rotary evaporator. The crude product was chromatographed on 300 g silica gel 60 (230-400 mesh) (hexane/diethyl ether=9/1).

12.3 g of 2-propynetetrahydro-2H-pyran-2-yl ether were obtained (GC: >95% purity).

Method based on: L. F. Tietze, Th. Eicher, *Reaktionen und Synthesen*, Georg Thieme Verlag Stuttgart, New York, $2^{nd}$ edition 1991, p. 211-212.

$^1$H-NMR (400 MHz, CDCl$_3$): δ=4.81 (t, J=3.3 Hz, 1H), 4.26 (dd, J=2.4 Hz and 24.7 Hz, 1H), 4.22 (dd, J=2.4 Hz and 24.7 Hz, 1H), 3.89-3.77 (m, 1H), 3.59-3.47 (m, 1H), 2.43 (t, J=2.4 Hz, 1H), 1.83-1.47 (m, 6H).

s: singlet, d: doublet, t: triplet, q: quartet, quin: quintet, m: multiplet, s$_b$: singlet broad, m$_c$: multiplet centred, OH: hydroxy group.

$^{13}$C-NMR (100 MHz, CDCl$_3$): δ=96.52 (CH), 79.63 (C), 73.90 (CH), 61.74, 53.81, 30.17, 25.34, 18.98 (CH$_2$).

Signal multiplicities determined by DEPT experiments.

FTIR (gas phase): 3328 (w), 2950 (m), 2879 (w), 1452 (w), 1350 (w), 1261 (w), 1202 (w), 1128 (m), 1038 (s), 954 (w), 904 (w), 874 (w), 816 (w).

s: strong, m: middle, w: weak.

MS (EI, 70 eV): 139 (M$^+$, 9), 101 (6), 85 (100), 82 (12), 67 (11), 56 (49), 41 (51), 39 (56), 29 (34).

2-Decynyltetrahydro-2H-pyran-2-yl ether (3)

100 ml n-BuLi (2.5 M in hexane) were added dropwise to a solution of 35.01 g 2-propynetetrahydro-2H-pyran-2-yl ether (0.25 mol) in 600 ml dry tetrahydrofuran (THF) under protective gas and with stirring at −80° C. in such a way that the temperature did not exceed −78° C. The temperature was allowed to rise to room temperature over 45 min, 9.3 g tetrabutylammonium iodide (TBAI) (25 mmol) and 56.5 g 1-heptyl iodide (0.25 mol) were added and the mixture was heated for 16 h with reflux.

The reaction was terminated by carefully adding 100 ml water. Dilution was performed with 500 ml diethyl ether and the organic phase was separated off, washed with saturated common salt solution and dried over sodium sulfate. The organic solvents were removed using a rotary evaporator and the crude product was distilled in a bulb tube.

38.5 g of a mixture of 19% 1-heptyl iodide, 26% decynol and 55% 2-decynyltetrahydro-2H-pyran-2-yl ether were obtained. This crude product was used without further purification for deprotection to 2-decyn-1-ol.

Method analogous to: M. Buck, J. M. Chong, *Tetrahedron Letters* 2001, 42, 5825-5827.

MS (EI, 70 eV): 237 (M$^+$, 0.5), 167 (2), 111 (11), 101 (32), 95 (46), 85 (100), 81 (51), 67 (48), 55 (48), 41 (50).

2-Decyn-1-ol (4)

The crude 2-decynyltetrahydro-2H-pyran-2-yl ether was heated with 100 ml water, 100 ml THF, 50 ml methanol and 2 ml hydrochloric acid (4 N) with reflux. Dilution was performed with 300 ml diethyl ether and the organic phase was separated off, washed with saturated common salt solution and dried over sodium sulfate. The organic solvents were removed using a rotary evaporator and the crude product distilled in a bulb tube.

25.2 g of 2-decyn-1-ol (purity according to GC: 85%; b.p.=approx. 120° C. at 5 mbar) were obtained.

Method based on: L. F. Tietze, Th. Eicher, *Reaktionen und Synthesen*, Georg Thieme Verlag Stuttgart, New York, 2nd edition 191, p. 413.

$^1$H-NMR (400 MHz, CDCl$_3$): δ=4.23 (s$_b$, 2 H), 2.63 (s$_b$, 1 H), 2.19 (tt, J=2.2 Hz and J=7.3 Hz, 2H), 1.49 (quint, J=7.3 Hz, 2H), 1.42-1.21 (m, 8H), 0.89 (t, J=6.8 Hz, 3H).

$^{13}$C-NMR (100 MHz, CDCl$_3$): δ=86.17 (C), 78.27 (C), 51.05, 31.73, 28.86, 28.82, 28.66, 22.64, 18.75 (CH$_2$), 14.06 (CH$_3$).

FTIR (gas phase): 3662 (w), 2938 (s), 2871 (m), 2285 (w), 2221 (w), 1460 (w), 1387 (m), 1137 (w), 1012 (m).

MS (EI, 70 eV): 153 (M$^+$, 0.5), 123 (11), 111 (17), 107 (16), 93 (45), 81 (61), 70 (64), 67 (88), 55 (100), 41 (99), 29 (50).

(Z)-2-Decen-1-ol (5)

20 g of crude 2-decyn-1-ol (85%, 110 mmol) and 4 g of Lindlar catalyst were stirred into 150 ml hexane under a hydrogen atmosphere at normal pressure. After 24 h, the mixture was filtered through silica gel 60 and the solvent removed using a rotary evaporator.

14.5 g of crude (Z)-2-decen-1-ol were obtained with a purity of 81.5%. (Impurities: 10% heptyl iodide, 8.5% decynol).

Method based on: K.-K. Chan, N. Cohen, J. P. De Noble, A. C. Specian Jr., G. Saucy, *J. Org. Chem.* 1950, 41, 3497-3505.

$^1$H-NMR (400 MHz, CDCl$_3$): δ=5.55 (m$_c$, 2 H), 4.18 (d, J=6.2 Hz, 2H), 2.06 (m$_c$, 2 H), 1.75 (s$_b$, 1 H), 1.43-1.20 (m, 10H), 0.89 (t, J=7.0 Hz, 3H).

$^{13}$C-NMR (100 MHz, CDCl$_3$): δ=132.5 (CH), 128.3 (CH), 58.28 (CH$_2$), 31.83, 29.64, 29.20, 29.17, 27.44, 22.66 (CH$_2$), 14.08 (CH$_3$).

FTIR (gas phase): 3659 (w), 3020 (w), 2934 (s), 2868 (m), ~1640 (w); 1462 (w), 1371 (w), 1024 (m).

MS (EI, 70 eV): 156 (M, 0.5), 138 (10), 109 (11), 95 (18), 81 (30), 67 (36), 57 (100), 41 (59), 29 (31)

cis-2-Heptylcyclopropyl-1-methanol (6)

100 ml diethyl zinc solution (1.0 M in hexane) and 100 ml dry diethyl ether were stirred under argon at −10° C. and 6.25 g (Z)-2-decen-1-ol (0.04 mol) in 20 ml diethyl ether were added dropwise in such a way that the temperature did not exceed 0° C. 8.1 ml of diiodomethane (0.1 mol) were added and stirred for 2 h at 0° C. and 16 h at room temperature.

The mixture was cooled to 0° C. and 100 ml of hydrochloric acid (4 N) were added. The organic phase was washed with 100 ml saturated sodium-hydrogen carbonate solution and 50 ml saturated common salt solution, dried over sodium sulfate and the solvent removed using a rotary evaporator. The crude product was distilled at approx. 130° C./7 mbar in a bulb tube. Chromatography was then carried out on silica gel 60 (hexane/ether=6/1).

3.4 g of cis-2-heptyl-cyclopropyl-1-methanol of 95% purity were obtained.

Method based on: T. Oshima, K. Kagechika, M. Adachi, M. Sodeoka, M. Shibasaki, *J. Am. Chem. Soc.* 1996, 118, 7108-7116.

$^1$H-NMR (400 MHz, CDCl$_3$): δ=3.59 (m$_c$, 2H), 2.26 (s$_b$, 1H), 1.50-1.16 (m, 12H), 1.08 (m$_c$, 1H), 0.88 (t, J=7.0 Hz, 3H), 0.87-0.80 (m, 1H), 0.69 (m$_c$, 1H), −0.040 (m$_c$, 1H).

$^{13}$C-NMR (100 MHz, CDCl$_3$): δ=62.96, 31.91, 30.18, 29.61, 29.34, 28.59, 22.69 (CH$_2$), 18.07, 16.18 (CH), 14.10 (CH$_3$), 9.55 (CH$_2$).

FTIR (gas phase): 3656 (w), 3071 (w), 3005 (w), 2933 (s), 2868 (m), 1463 (w), 1403 (w), 1353 (w), 1030 (m).

MS (EI, 70 eV): 152 (1), 129 (14), 111 (21), 95 (12), 81 (31), 69 (100), 57 (57), 55 (76), 43 (61), 41 (80), 29 (35).

cis-2-Heptylcyclopropyl-1-carboxylic acid (7)

2.5 g chromium trioxide (25 mmol) were dissolved in 60 ml sulfuric acid (1 M, 60 mmol, 2.4 eq). 2.1 g cis-2-heptyl-cyclopropyl-1-methanol in 100 ml acetone were added dropwise, with stirring, within 1 h at 0° C. The mixture was stirred for 18 h at room temperature.

300 ml of diethyl ether were added and the phases were separated. The aqueous phase was extracted three times with 100 ml diethyl ether each time, the organic phases were combined and washed three times with 50 ml saturated common salt solution each time.

The organic acid was separated by washing four times with 50 ml sodium hydroxide solution (5%) each time. It was washed twice with 50 ml diethyl ether and the acid was released with 150 ml hydrochloric acid (4 N). Extraction was performed five times with 100 ml diethyl ether each time. The organic phase was washed with 50 ml saturated sodium chloride solution and dried over sodium sulfate.

After concentrating using a rotary evaporator, the crude product was chromatographed on silica gel 60 (cyclohexane/diethyl ether=3/1).

0.72 g of cis-2-heptyl-cyclopropyl-1-carboxylic acid were obtained with a purity of >98% (GC).

Method analogous to: J. G. Millar, A. C. Oehlschlager, J. W. Wong, *J. Org. Chem.* 1983, 48, 4404-4407.

$^1$H-NMR (400 MHz, CDCl$_3$): δ=11.8 (s$_b$, 1 H), 1.65 (m$_c$, 1 H), 1.55 (m$_c$, 1 H), 1.48-1.15 (m, 12H), 1.06 (m$_c$, 1 H), 0.96 (m$_c$, 1 H), 0.88 (t, J=6.4 Hz, 3 H).

$^{13}$C-NMR (100 MHz, CDCl$_3$): δ=179.8 (COO), 31.85, 29.54, 29.28, 29.26, 26.92 (CH$_2$), 23.22 (CH), 22.68 (CH$_2$), 18.13 (CH), 14.44 (CH$_2$), 14.09 (CH$_3$).

FTIR (gas phase): 3580 (m), 3016 (w), 2967 (m), 2934 (s), 2869 (m), 1767 (s), 1458 (w), 1414 (w), 1367 (w), 1175 (w), 1133 (s), 883 (w).

MS (EI, 70 eV): 137 (6), 123 (11), 114 (11), 99 (21), 84 (36), 73 (100), 69 (41), 55 (73), 43 (48), 41 (62), 29 (32).

EXAMPLE 2

Synthesis of trans-2-heptylcyclopropyl-1-carboxylic acid (12)

Figure 2:
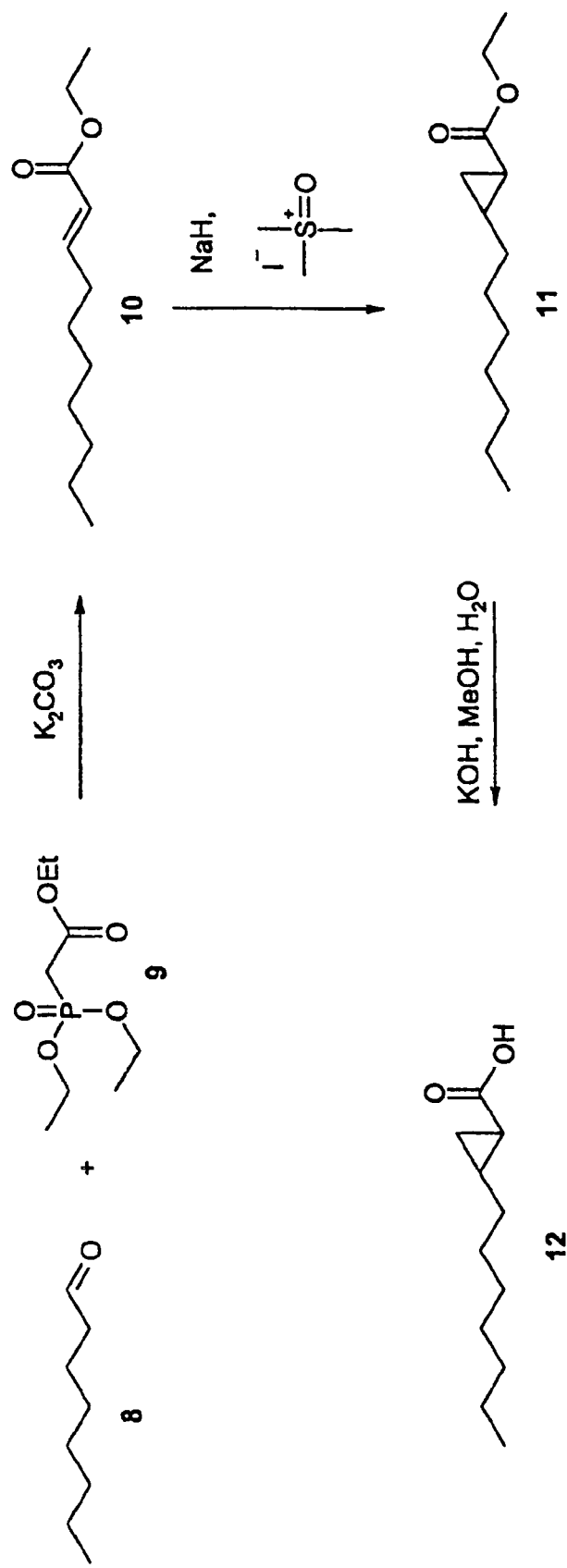
FIG. 2 shows the synthesis of trans-2-heptylcyclopropyl-1-carboxylic acid (12).

The synthesis is illustrated diagrammatically in FIG. 2.

Wittig-Horner reaction of octanal with triethyl phosphonoacetate yields (E)-2-decenoic acid ethyl ester. (On stereoselectivity cp.: J. Villieras, M. Rambaud, *Synthesis* 1983, 300-303; R. Brückner, *Reaktionsmechanismen*, Spektrum Akademischer Verlag, Heidelberg, Berlin, Oxford, 1$^{st}$ edition 1996, p. 321). By cyclopropanation with dimethylsulfoxonium methylide, trans-2-heptylcyclopropyl-1-carboxylic acid ethyl ester is obtained selectively. (On stereoselectivity: according to S. R. Landor, N. Punja, *J. Org. Chem.* 1967, 2495-2500, (E)-configured α,β-unsaturated esters lead to trans-substituted cyclopropanes; (Z)-configured α,β-unsaturated esters were not investigated. According to R. Brückner, *Reaktionsmechanismen*, Spektrum Akademischer Verlag, Heidelberg, Berlin, Oxford, 1$^{st}$ edition 1996, p. 321, both (E)- and (Z)-configured α,β-unsaturated esters yield trans-substituted cyclopropanes). Mild saponification with potassium hydroxide at room temperature gives trans-2-heptylcyclopropyl-1-carboxylic acid.

(E)-2-Decenoic acid ethyl ester (10)

50.5 g of triethyl phosphonoacetate (9) (0.225 mol) were added dropwise to 150 g iced water and 62.0 g potassium carbonate (0.45 mol) within 5 min, and then, within 30 min, 19.23 g of octanal (8) (0.15 mol) were added dropwise. The temperature should not exceed 15° C. The mixture was stirred for 20 h at room temperature.

350 ml of hexane were added, the organic phase was separated off and washed twice with 150 ml water each time and once with 100 ml saturated common salt solution. Drying was performed over sodium sulfate and the solvent was evaporated using a rotary evaporator. The crude product was distilled in a bulb tube at 180-185° C./6-7 mbar.

27.4 g of (Z)-2-decenoic acid ethyl ester of >95% purity were obtained.

Literature: J. Villieras, M. Rambaud, *Synthesis* 1983, 300-303.

$^1$H-NMR (400 MHz, CDCl$_3$): δ=6.95 (dt, J=7.0 Hz and 15.8 Hz, 1H), 5.79 (dt, J=15.4 Hz and 1.5 Hz, 1H), 4.17 (q, J=7.0 Hz, 2H), 2.18 (dq, J=1.5 Hz and 7.0 Hz, 2H), 1.46 (m$_c$, 1 H), 1.38-1.22 (m, 12H), 0.88 (t, 3H).

$^{13}$C-NMR (100 MHz, CDCl$_3$): δ=166.3 (COO), 149.0 (CH), 121.1 (CH), 59.93, 32.20, 31.82, 29.14, 29.09, 28.08, 22.66 (CH$_2$), 14.29, 14.06 (CH$_3$).

FTIR (gas phase): ~2966 (m), 2937 (s), 2868 (m), 1740 (s), 1656 (w) 1464 (w), 1370 (w), 1310 (m), 1260 (s), 1167 (s), 1124 (w), 1047 (m), 978 (w), 858 (w).

MS (EI, 70 eV): 153 (61), 127 (20), 115 (20), 110 (41), 101 (76), 88 (38), 84 (40), 73 (85), 69 (57), 55 (100), 41 (83), 29 (73).

trans-2-Heptylcyclopropyl-1-carboxylic acid ethyl ester (11)

Under protective gas, 0.84 g of sodium hydride (35.0 mmol) were suspended in 25 ml dry dimethyl sulfoxide and 6.60 g trimethylsulfoxonium iodide were added. The mixture was stirred for 30 min, during which time vigorous gas generation and a slight rise in temperature could be observed. 4.96 g of (E)-2-decenoic acid ethyl ester (25 mmol) were added over 15 min and the mixture was stirred for 150 min at room temperature.

100 ml of water were carefully added and the mixture was diluted with 500 ml diethyl ether. The organic phase was separated off, washed with saturated sodium chloride solution, dried over sodium sulfate and the diethyl ether removed using a rotary evaporator.

The crude product was chromatographed on silica gel 60 (hexane/diethyl ether=6/1).

1.1 g of trans-2-heptyl-cyclopropyl-1-carboxylic acid ethyl ester were obtained.

Method analogous to: S. R. Landor, N. Punja, *J. Chem. Soc.* 1967, 2495-2500.

$^1$H-NMR (400 MHz, CDCl$_3$): δ=4.10 (q, J=7.2 Hz, 2H), 1.45-1.22 (m, 17H), 1.13 (m$_c$, 1 H), 0.86 (t, 3H, J=7.0 Hz), 0.67 (m$_c$, 1 H).

$^{13}$C-NMR (100 MHz, CDCl$_3$): δ=174.1 (COO), 60.11, 33.07, 31.84, 29.27, 29.21, 29.11 (CH$_2$), 22.87 (CH), 22.66 (CH$_2$), 20.22 (CH), 15.45 (CH$_2$), 14.29, 14.08 (CH$_3$).

FTIR (gas phase): 2966 (m), 2933 (s), 2865 (m), 1745 (s), 1456 (w), 1410 (w), 1371 (w), 1339 (w), 1259 (m), 1171 (s), 1083 (w), 1046 (w), 861 (w).

MS (EI, 70 eV): 212 (M, 1), 167 (23), 128 (39), 123 (14), 101 (91), 99 (33), 88 (40), 81 (32), 73 (80), 69 (52), 55 (100), 41 (65), 29 (54).

trans-2-Heptylcyclopropyl-1-carboxylic acid (12)

900 mg of trans-2-heptyl-cyclopropyl-1-carboxylic acid ethyl ester (4.24 mmol) were stirred with 720 mg potassium hydroxide (12.8 mmol) in 2 ml water and 3 ml ethanol for 4.5 h at room temperature. Using dilute hydrochloric acid (1 M), pH=2 was established and the aqueous phase was extracted three times with 30 ml diethyl ether each time. The mixture was washed with 20 ml saturated sodium chloride solution, dried over sodium sulfate and the solvents were distilled off using a rotary evaporator.

780 mg of trans-2-heptyl-cyclopropyl-1-carboxylic acid were obtained with a purity of >98% (GC).

Method based on: L. F. Tietze, Th. Eicher, *Reaktionen und Synthesen*, Georg Thieme Verlag Stuttgart, New York, 2$^{nd}$ edition 191, p. 491-492.

$^1$H-NMR (400 MHz, CDCl$_3$): δ=8.72 (s$_b$, 1 H), 1.50-1.17 (m, 15H), 0.88 (t, J=6.8 Hz, 3H), 0.74 (ddd, J=4.0, 6.6, 10.6 Hz, 1H).

$^{13}$C-NMR (100 MHz, CDCl$_3$): δ=180.6 (COO), 33.01, 31.78, 29.20, 29.20. 29.02 (CH$_2$), 23.97 (CH), 22.63 (CH$_2$), 20.10 (CH), 16.32 (CH$_2$), 14.06 (CH$_3$)

FTIR (gas phase): 3580 (m), 3016 (w), 2967 (m), 2934 (s), 2866 (m), 1767 (s), 1458 (w), 1415 (w), 1366 (w), 1175 (w), 1132 (s).

MS (EI, 70 eV): 138 (3), 124 (14), 113 (15), 99 (23), 84 (38), 73 (100), 69 (55), 55 (86), 43 (60), 41 (75), 29 (37).

EXAMPLE 3

Sensory Investigations of
cis-2-heptylcyclopropyl-1-carboxylic acid and
trans-2-heptylcyclopropyl-1-carboxylic acid The compound comprises 2 diastereomers each with 2 enantiomers. The two racemic diastereomers clearly differ in their odour properties. The cis isomer has a distinctly lower odour threshold than the trans isomer.

cis-2-Heptylcyclopropyl-1-carboxylic acid (racemic)

Odour Description:
woody, balsamic, incense-like, green, herbal, pith-like, waxy
Odour Threshold in Water:
3 ppb (3 µg/l water)

trans-2-Heptylcyclopropyl-1-carboxylic acid (racemic)

Odour Description:
Waxy, fatty, sweet
Odour Threshold in Water:
100 ppb (100 µg/l water)

EXAMPLE 4

Flavour Formulation

TABLE 1

|  | Quantity [%] | |
| --- | --- | --- |
| Component | A | B |
| Orange oil, Brazilian green | 40 | 40 |
| cis-2-Heptylcyclopropyl-1-carboxylic acid | — | 0.1 |
| Ethyl butyrate | 2 | 2 |
| Aldehyde C 12 | 0.03 | 0.03 |
| Aldehyde C10 | 0.05 | 0.05 |
| Linalool | 0.2 | 0.2 |
| Orange oil Florida | 15 | 15 |
| Orange essence oil | 42.72 | 42.62 |
| Total | 100 | 100 |

A conventional flavour composition (composition A) was compared with a flavour composition according to the invention (composition B). As can be seen from Table 1 above, composition B largely corresponded to composition A but, unlike composition A, composition B contained a proportion of 0.1% cis-2-heptylcyclopropyl-1-carboxylic acid (based on the total mass of the composition), which was balanced by a reduction in the proportion of orange essence oil.

The flavour of the composition according to the invention was fresher, fruitier, fuller and more peel-like compared with the flavour of the conventional composition A.

EXAMPLE 5

Synthesis of Enantiomer-Enriched
cis-2-heptylcyclopropyl-1-carboxylic acid (1S,2R)

Preparation of the dioxoborolane ligand (13)

10.00 g of n-butylboronic acid (98.10 mmol) were added to a solution of 16.39 g (+)-N,N,N',N'-tetramethyl-L-tartaric acid diamide (80.27 mmol, Aldrich batch 11410TA) in 110 ml dry toluene and boiled for 8 hours in a water separator. The solvent was distilled off under reduced pressure and 10 ml of dichloromethane were added to the residue. This was filtered off from the remaining crystals, rinsed with 5 ml dichloromethane and the solvent was removed under reduced pressure using a rotary evaporator. 22.0 g of (13) were obtained as a clear, colourless oil.

$^1$H-NMR (400 MHz, CDCl$_3$): δ=5.53 (s, 2H), 3.20 (s, 6H), 2.98 (s, 6H) 1.42-1.28 (m, 4H), 0.89-0.83 (m, 5H).

$^{13}$C-NMR (100 MHz, CDCl$_3$): δ=168.0, 75.56, 37.05, 35.89, 25.82, 25.17, 13.80, 9.99.

Preparation of the Zn(CH$_2$I)$_2$ DME Complex (14) as a Solution in CH$_2$Cl$_2$ 37 ml of dichloromethane were placed under protective gas with 3.5 g of molecular sieve. This was cooled to −20° C. and the following were added consecutively, with stirring: 18.7 ml diethyl zinc (1.0 M in hexane, 18.7 mmol), 1.95 ml ethylene glycol dimethyl ether (DME, 18.7 mmol) and 3.0 ml diiodomethane (37.5 mmol). The mixture was stirred for 30 min at −20° C. The clear solution of (14) was used directly for the cyclopropanation.

Enantioselective Cyclopropanation of (Z)-2-decen-1-ol (5)

Under protective gas, a mixture of 2.20 g of the dioxoborolane ligand (13), 1.17 g of 2-decen-1-ol (5), 3.4 g of molecular sieve 4 Å and 37 ml of dry diethyl ether was prepared and cooled to −20° C. Using a Teflon cannula, the freshly prepared $Zn(CH_2I_2)$ DME complex (14) was added within 2 min at −20° C. The mixture was stirred for 2 hours at −10° C. and then 15 ml of saturated ammonium chloride solution were added. The solid was filtered off, the organic phase separated and the aqueous phase extracted three times with 10 ml diethyl ether each time. The combined organic phases were stirred for 12 h with 100 ml sodium hydroxide solution (5 M). The organic phase was separated off, extracted with 20 ml dilute hydrochloric acid, saturated sodium hydrogen carbonate and common salt solution in succession and dried over sodium sulfate. After evaporating off the solvent, 3.57 g of a yellow oil were obtained. The crude product was chromatographed on silica gel with a solvent of diethyl ether/hexane=1/8. 0.8 g of a colourless oil of (15) were obtained.

Literature: A. B. Charette, S. Prescott, C. Brochu, *J. Org. Chem.* 1995, 60, 1081-1083.

Determination of the Enantiomeric Excess Via Mosher Ester (17)

To validate the method, the racemic mixture of the cis-2-heptylcyclopropyl-1-methanol (6) was first reacted. After it had been ensured that the diastereotopic protons produce $1'-H_2$ offset signals, 33.1 mg of the enantiomer-enriched heptylcyclopropyl-1-methanol (15) were reacted as follows:

33.1 mg of the alcohol (15) were dissolved in 0.5 ml dichloromethane and 0.36 ml pyridine and stirred with 49.1 mg (R)-(−)-α-methoxy-α-(trifluoromethyl)phenylacetyl chloride (16) for 24 h at RT. The precipitated salts were filtered off using silica gel and the solvent removed in vacuo. Approx. 50 mg of a yellowish oil (17) were obtained. In the $^1H$ spectrum, measured at a field strength of 400 MHz in $CDCl_3$, the $1'-H_2$ signals of the two diastereomers were detected separately from one another (diastereomer 1: 4.49 ppm, dd, J=7.2, 11.4 Hz, 4.15 ppm, dd, J=8.5, 11.6 Hz; diastereomer 2: 4.44 ppm, dd, J=7.2, 11.4 Hz, 4.22 ppm, dd, J=8.5, 11.6 Hz). From the integration, a diastereomer ratio in the range of 95/5-88/12 is obtained.

Enantiomer-Enriched cis-2-heptylcyclopropyl-1-carboxylic acid (18)

1.35 g of chromium trioxide (13.5 mmol) were dissolved in 9.5 ml sulfuric acid (2 M, 19 mmol). 0.5 g of enantiomer-enriched (Z)-2-heptyl-cyclopropyl-1-methanol (15) in 5 ml acetone were added dropwise at RT, with stirring. Stirring was performed for 38 h at RT. 200 ml of diethyl ether were added and the phases were separated. The organic phase was extracted three times with 50 ml of 5% sodium hydroxide solution each time, and this was shaken up three times together with 100 ml of diethyl ether each time. Acidification was performed with 10% hydrochloric acid to pH=1 and the carboxylic acid was separated off by extracting three times with 100 ml of diethyl ether each time. After concentrating using a rotary evaporator, the crude product was purified by chromatography on 90 g silica gel 60 (230-400 mesh; hexane/diethyl ether=8/1). 0.4 g of (18) were obtained with approx. 83% purity (GC). By chiral gas chromatography on an IVADEX-3 GC column under the conditions given in Example 6, an enantiomeric excess of ee=92% was determined for the (1S,2R) enantiomer.

Determination of the Direction of Optical Rotation for the Enantiomer-Enriched cis-2-heptylcyclopropyl-1-carboxylic acid (18)

The direction of optical rotation of the enantiomer-enriched material (18) was determined using a chiralyser. For this purpose, the material was first purified further by preparative HPLC:

Column: Kromasil-100 C18; 5μ; 250×8 mm
Mobile phase: A: Methanol;
B: $H_2O$ pH=3 (formic acid), isocratic 80% A, 20% B After preparative HPLC, a material (18) with 98% purity according to GC was obtained. After calibrating the chiralyser with (−)-fructose and (+)-glucose, the purified material (18) was measured with the chiralyser. The direction of rotation was determined as (+).

EXAMPLE 6

Isolation of Naturally Occurring 2-heptylcyclopropyl-1-carboxylic acid and the Analysis Thereof The starting substance was orange residue, which is obtained from orange peel oil. The proportion of residue in a peel oil is generally in the range of a few wt. %, typically in the range of 1 to 5 wt. %.

By acid-base separation, 1.2 g of an acid fraction were obtained from 500 g of orange residue. The acid fraction was derivatised using diazomethane and the resulting methyl esters were separated by HPLC. By means of this HPLC separation, 65 mg of a fraction were obtained which mainly contained cascarillic acid methyl ester. The content of cascarillic acid in the orange residue was therefore approx. 130 ppm.

2-Heptylcyclopropyl-1-carboxylic acid was detected sensorially (by olfactory GC) for the first time in a fraction enriched in cascarillic acid. No corresponding peak in the GC was shown. By repeated enrichment in 2-heptylcyclopropyl-1-carboxylic acid, it was possible to obtain a fraction consisting mainly of cascarillic acid and 2-heptylcyclopropyl-1-carboxylic acid. The gas-chromatographic ratio of the peaks of cascarillic acid and 2-heptylcyclopropyl-1-carboxylic acid in the repeatedly enriched fraction was about 99:1. In total, there proved to be a content of 2-heptylcyclopropyl-1-carboxylic acid of about 1 ppb in the orange residue.

The investigations were performed by chiral GC and by olfactory GC (ODP; olfactometry).

Agilent GC 6890 with Gerstel KAS 4 injector and Agilent 66676 Autosampler

Column: 25 m×0.25 mm ID, FT 0.15 mm FT IVADEX-3 (Iva Analysentechnik)
Temperature/oven: 80° C. with 2° C./min up to 160° C.
Carrier gas: He, 1.5 ml/min
Detector: FID (flame ionisation detector) and ODP (olfactometric determination)
Sample: each 1 μl; split 1:20. 0.01% in ether The following absolute stereochemistry could be assigned to the individual GC peaks:
1st peak: (1S,2R)-cis isomer, formula C
2nd peak: (1R,2S)-cis isomer, formula B
3rd peak: (1R,2R)-trans isomer, formula D
4th peak: (1S,2S)-trans isomer, formula E It was found that the naturally occurring 2-heptylcyclopropyl-1-carboxylic acid corresponds to formula C and has the absolute configuration (1S,2R):

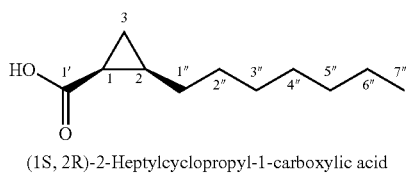

(1S, 2R)-2-Heptylcyclopropyl-1-carboxylic acid

EXAMPLE 7

Synthesis of Mixtures of
cis-2-heptylcyclopropyl-1-carboxylic acid and
trans-2-heptylcyclopropyl-1-carboxylic acid 2-Heptylcyclopropyl-1-carboxylic acid ethyl ester by Transition-Metal-Catalysed Reaction of 1-nonene with ethyl diazoacetate With Rhodium Acetate as Catalyst:

140.8 g of 1-nonene (1.116 mol) and 456 g of rhodium(II) acetate dimer (1.03 mmol) were initially charged into a 500 ml three-neck flask with a gas-tight stirrer, internal thermometer and gas meter. The reaction mixture was heated to 40° C. and 50.8 g of ethyl diazoacetate (445 mmol) were metered in over 8 h at a constant rate. The immediate conversion of the diazoacetate that had been added dropwise could be monitored by comparing the measured volume of gas with the theoretical value of released nitrogen.

The catalyst was filtered off and the excess 1-nonene was recovered by distillation using a rotary evaporator under reduced pressure. The remaining oil contained approx. 2.5% ethyl maleate, approx. 2.5% fumarate, approx. 39% cis-heptylcyclopropyl-1-carboxylic acid ethyl ester and approx 56% trans-heptylcyclopropyl-1-carboxylic acid ester according to GC. The crude heptylcyclopropyl-1-carboxylic acid ethyl ester could be purified by fractional distillation in a high vacuum. During this process, it was possible to adjust the cis/trans ratio by selection of appropriate fractions.

With Activated Copper Bronze as Catalyst:

1.00 g of copper bronze was initially charged into a 100 ml three-neck flask with a magnetic stirrer, reflux condenser, pneumatic trough with a graduated glass tube, internal thermometer and septum and stirred for 30 min in 2 ml glacial acetic acid. The metal powder was allowed to settle and the acetic acid was carefully drawn off using a syringe cannula.

29.0 g of 1-nonene (230 mmol) were added and the reaction mixture was heated to 85° C. 2.00 g of ethyl diazoacetate (17.5 mmol) were metered in over 2 h at a constant rate. The immediate conversion of the diazoacetate that had been added dropwise could be monitored by comparing the measured volume of gas with the theoretical value of released nitrogen. According to GC, cis-heptylcyclopropyl-1-carboxylic acid ethyl ester and trans-heptylcyclopropyl-1-carboxylic acid ester were contained in the crude product in a ratio of 37/63.

Literature: L. A. Paquette et al., *J. Am. Chem. Soc.* 1969, 91, 7108-7113; P. H. Mazzocchi et al., *J. Org. Chem.* 1973, 38, 2221-2225.

2-Heptylcyclopropyl-1-carboxylic acid by Saponification of 2-heptylcyclopropyl-1-carboxylic acid ethyl ester A solution of 31.7 g KOH or NaOH in 50 ml water was initially charged into a 500 ml three-neck flask, diluted with 150 ml ethanol and 60 g of cis/trans-heptylcyclopropyl-1-carboxylic acid ester were added slowly, with stirring. Stirring was performed for 18 h at room temperature. By reducing the reaction period, the cis/trans proportion of heptylcyclopropyl-1-carboxylic acid can be adjusted.

Using a rotary evaporator, approx. 100 ml ethanol were removed and taken up in a mixture of 100 ml water, 50 ml saturated common salt solution, 300 ml tert.-butyl methyl ester and 20 ml n-hexane. The aqueous phase was separated off and adjusted to pH=1 with 10% HCl. Extraction was performed three times with 150 ml tert.-butyl methyl ester each time and the combined organic phases were dried over sodium sulfate. After removing the solvent using a rotary evaporator, distillation was performed on a 20 cm Vigreux column in vacuo. The cis/trans ratio could be adjusted by selecting suitable fractions.

EXAMPLE 8

Synthesis of Enantiomer-Enriched
cis-2-heptylcyclopropyl-1-carboxylic acid (1R,2S)

(2S)-2-Heptylcyclopropyl-1,1-dicarboxylic acid diethyl ester by Reaction of ethyl malonate with (4R)-4-heptyl-[1,3,2]dioxathiolane 2,2-dioxide (4R)-4-Heptyl-[1,3,2]dioxathiolane 2,2-dioxide was prepared in three steps according to the specifications of K. B. Sharpless (H. C. Kolb, M. S. VanNieuwenhze, K. B. Sharpless, *Chem. Rev.* 1994, 94, 2483-2547; Y. Gao, K. B. Sharpless, *J. Am. Chem. Soc.* 1988, 110, 7538-7539) from 1-nonene by cis-hydroxylation with $(DHQD)_2PHAL$ ligands (AD-Mix beta), reaction with thionyl chloride and subsequent oxidation to the cyclic sulfate with ruthenium catalysis.

0.25 g of sodium hydride (10.4 mmol) in 20 ml DMF were initially charged into a 50 ml two-neck flask with a reflux condenser, magnetic stirrer and septum and 0.80 g diethyl malonate (5.00 mmol) were slowly added dropwise, with stirring. Once gas generation had finished, 1.00 g (4R)-4-heptyl-[1,3,2]dioxathiolane-2,2-dioxide (4.50 mmol) was added slowly. The mixture was stirred for 30 min at room temperature and 30 min with reflux. Stirring was continued for 14 h at room temperature, 50 ml water were added and extraction was performed three times with 50 ml tert.-butyl methyl ether. The organic phase was washed with 30 ml of 10% HCl solution, 30 ml of 10% sodium hydrogen carbonate solution and 30 ml of saturated common salt solution, dried over sodium sulfate and the solvent removed using a rotary evaporator.

1.32 g of a colourless oil were obtained with 87% 2-heptylcyclopropyl-1,1-dicarboxylic acid diethyl ester according to GC.

Literature: Y. Gao, K. B. Sharpless, *J. Am. Chem. Soc.* 1988, 110, 7538-7539.

2-Heptylcyclopropyl-1-carboxylic acid ethyl ester by Decarboxylation of 2-heptylcyclopropyl-1,1-dicarboxylic acid diethyl ester with Lithium Chloride in DMSO 300 mg 2-heptylcyclopropyl-1,1-dicarboxylic acid diethyl ester (1.05 mmol), 45 mg lithium chloride (1.05 mmol) and 40 mg water (2.22 mmol) in 9 ml DMSO were initially charged into a 25 ml two-neck flask and heated with reflux for 8 h.

10 ml water were added and extraction was performed with 50 ml tert.-butyl methyl ether. The organic phase was washed with 10 ml water and 10 ml saturated common salt solution, dried over sodium sulfate and the solvent removed in vacuo. 205 mg of a yellowish oil were obtained. According to GC, 17% cis- and 21% trans-2-heptylcyclopropyl-1-carboxylic acid ethyl ester were contained.

Literature: H. Markgraf et al., *J. Org. Chem.* 1977, 42, 2631-2632.

Before the mixture of cis- and trans-2-heptylcyclopropyl-1-carboxylic acid ethyl ester thus obtained was fed into the saponification, a further chromatographic purification took place on Ag-doped silica gel.

2-Heptylcyclopropyl-1-carboxylic acid by Saponification of 2-heptylcyclopropyl-1-carboxylic acid ethyl ester The saponification took place as described in Example 7.

By chiral gas chromatography on an IVADEX-3 GC column under the conditions given in Example 6, an enantiomeric excess of ee=77% was determined for the (1R,2S) enantiomer. This non-natural cis enantiomer of formula B displays a very much weaker odour than the naturally occurring (1S,2R) enantiomer of formula C.

EXAMPLE 8

Application Examples

Example 8.1

Natural (1S,2R) 2-heptylcyclopropyl-1-carboxylic acid (formula C) was added to a drink in combination with selected citrus flavourings in a concentration of 5 to 10 ppb. In comparison with the drink without an additive, the drink with an additive was evaluated sensorially as follows: "more body, more fruity, more impact". Stability tests also displayed an improvement in terms of taste retention.

Example 8.2

Combinations of (1S,2R) 2-heptylcyclopropyl-1-carboxylic acid (formula C) with (Z)-8-tetradecenal and 4,5-epoxy-(E)-2-decenal also displayed an improved taste performance.

The invention claimed is:

1. A formulation having a flavor or aroma comprising an isolated and/or purified enantiomer of 2-heptylcyclopropyl-1-carboxylic acid or a mixture of two, three or all enantiomers of 2-heptylcyclopropyl-1-carboxylic acid.

2. A formulation having a flavor or aroma comprising a mixture of the two enantiomers of cis-2-heptylcyclopropyl-1-carboxylic acid or the two enantiomers of trans-2-heptylcyclopropyl-1-carboxylic acid.

3. The formulation according to claim 2, further comprising an enantiomeric excess of at least 40% of said cis-2-heptylcyclopropyl-1-carboxylic acid or said trans-2-heptylcyclopropyl-1-carboxylic acid.

4. Perfume composition and/or flavouring composition, containing an organoleptically active quantity of an isolated and/or purified enantiomer or mixture of enantiomers of claim 1.

5. Perfume composition and/or flavouring composition, containing a proportion of at least 0.001 wt. % of an enantiomer of 2-heptylcyclopropyl-1-carboxylic acid or a mixture of two, three or all enantiomers of 2-heptylcyclopropyl-1-carboxylic acid, based on the total mass of the perfume composition or flavouring composition.

6. Flavoured foodstuff, containing an organoleptically active quantity of an isolated or purified enantiomer of 2-heptylcyclopropyl-1-carboxylic acid or a mixture of two, three or all enantiomers of 2-heptylcyclopropyl-1-carboxylic acid.

7. Body care product, cleaning agent or other product not intended for consumption, containing an organoleptically active quantity of an enantiomer of 2-heptylcyclopropyl-1-carboxylic acid or a mixture of two, three or all enantiomers of 2-heptylcyclopropyl-1-carboxylic acid.

8. A method for enhancing aroma and/or flavor sensory impression of a product by adding to said product an enantiomer or mixture of enantiomers of claim 1.

9. Process for the production or modification of a perfume composition or flavouring composition, with the following steps:
preparing a starting composition, and
mixing the starting composition with an organoleptically active quantity of an enantiomer or mixture of enantiomers of claim 1.

10. Process for the modification of a flavouring composition in a fresher, fruitier, fuller and/or more peel-like direction, wherein the flavouring composition is mixed with an organoleptically active quantity of an enantiomer or mixture of the two enantiomers of cis-2-heptylcyclopropyl-1-carboxylic acid.

11. Process for the selective preparation of cis- or trans-2-heptylcyclopropyl-1-carboxylic acid, wherein, a precursor with a Z- or E-configured double bond is selectively cyclopropanated to establish the cis or trans configuration of the substituents on the cyclopropane ring.

12. Perfume composition and/or flavouring composition according to claim 5, containing a proportion of at least 0.01 wt. % of said enantiomer or of said mixture of enantiomers, based on the total mass of the perfume composition or flavouring composition.

13. Perfume composition and/or flavouring composition according to claim 12, containing a proportion of at least 0.1 wt. % of said enantiomer or of said mixture of enantiomers, based on the total mass of the perfume composition or flavouring composition.

14. The method according to claim 8 wherein flavor of said product is enhanced by adding said enantiomer or mixture of enantiomers.

15. The method according to claim 8 wherein aroma of said product is enhanced by adding said enantiomer or mixture of enantiomers.

16. The method of claim 8, wherein said enantiomer is a mixture of cis-2-heptylcyclopropyl-1-carboxylic acid and trans-2-heptylcyclopropyl-1-carboxylic acid.

17. The method of claim 8, wherein said enantiomer is a racemic mixture of cis-2-heptylcyclopropyl-1-carboxylic acid, and where said enantiomer is added in an amount to impart a woody, balsamic, incense-like, green herbal, pith-like and waxy aroma.

18. The method of claim 8, wherein said enantiomer is a racemic mixture of trans-2-heptylcyclopropyl-1-carboxylic acid.

19. The method of claim 8, wherein said enantiomers are cis-enantiomers and are added in an amount to provide balsamic flavor without an aldehyde flavor note.

20. The method of claim 8, wherein said enantiomers are trans-enantiomers and are added in an amount to provide a waxy, fatty or sweet perfume note to said product.

* * * * *